United States Patent
Sing et al.

(10) Patent No.: US 9,623,089 B2
(45) Date of Patent: *Apr. 18, 2017

(54) METHODS FOR ACCELERATING THE HEALING OF CONNECTIVE TISSUE INJURIES AND DISORDERS

(71) Applicant: Stemnion, Inc., Pittsburgh, PA (US)

(72) Inventors: George L Sing, New York, NY (US); David L Steed, Pittsburgh, PA (US)

(73) Assignee: STEMNION, INC., Pittsburgh, PA (US)

( * ) Notice: Subject to any disclaimer, the term of this patent is extended or adjusted under 35 U.S.C. 154(b) by 41 days.

This patent is subject to a terminal disclaimer.

(21) Appl. No.: 14/525,654

(22) Filed: Oct. 28, 2014

(65) Prior Publication Data

US 2016/0114008 A1    Apr. 28, 2016

(51) Int. Cl.

| | | |
|---|---|---|
| A61K 38/18 | (2006.01) |
| A61K 38/46 | (2006.01) |
| A61K 35/50 | (2015.01) |
| A61K 31/407 | (2006.01) |
| A61K 31/56 | (2006.01) |
| A61K 35/12 | (2015.01) |
| A61K 38/19 | (2006.01) |
| A61K 39/395 | (2006.01) |
| A61K 45/06 | (2006.01) |
| A61K 38/57 | (2006.01) |

(52) U.S. Cl.
CPC .......... *A61K 38/465* (2013.01); *A61K 31/407* (2013.01); *A61K 31/56* (2013.01); *A61K 35/12* (2013.01); *A61K 35/50* (2013.01); *A61K 38/18* (2013.01); *A61K 38/1841* (2013.01); *A61K 38/1858* (2013.01); *A61K 38/1866* (2013.01); *A61K 38/19* (2013.01); *A61K 38/57* (2013.01); *A61K 39/395* (2013.01); *A61K 45/06* (2013.01); *C12Y 301/27* (2013.01)

(58) Field of Classification Search
CPC ............ A61K 38/1858; A61K 38/1866; A61K 38/1841; A61K 38/18; A61K 2300/00
See application file for complete search history.

(56) References Cited

U.S. PATENT DOCUMENTS

| | | | |
|---|---|---|---|
| 6,514,514 B1 * | 2/2003 | Atkinson | A61K 9/5153 |
| | | | 424/422 |
| 8,541,027 B2 * | 9/2013 | Wright | A61L 31/048 |
| | | | 424/484 |
| 2005/0261617 A1 | 11/2005 | Hall | |
| 2006/0222634 A1 | 10/2006 | Clarke et al. | |
| 2007/0231297 A1 | 10/2007 | Smith et al. | |
| 2009/0010899 A1 | 1/2009 | Palladino et al. | |
| 2009/0093056 A1 | 4/2009 | Itskovitz-Eldor et al. | |
| 2010/0068180 A1 | 3/2010 | Marshall et al. | |
| 2010/0080779 A1 | 4/2010 | Smith et al. | |
| 2010/0144604 A1 | 6/2010 | Marshall et al. | |
| 2010/0215731 A1 * | 8/2010 | Emans | A61K 9/0024 |
| | | | 514/1.1 |
| 2011/0129544 A1 * | 6/2011 | Miyazaki | A61K 31/726 |
| | | | 424/602 |
| 2013/0330391 A1 * | 12/2013 | Malinin | A61F 2/30756 |
| | | | 424/423 |

OTHER PUBLICATIONS

Sharma, P., et al., 2008, Disability and Rehabilation 30(20-22):1733-1745.
Chen, X., et al., 2009, Stem Cells 27:1276-1287.
Nourissat, G., et al., 2010 Plos One 5(8):e12248.
Tapp, H., et al., 2009, Exp Biolo Med 234:1-9.

* cited by examiner

*Primary Examiner* — Daniel C Gamett
(74) *Attorney, Agent, or Firm* — Linda O. Palladino; Gail M. Kempler

(57) ABSTRACT

The invention is directed to methods for accelerating the healing of connective tissue injuries and disorders. In particular, the invention is directed to accelerating the healing of injuries and disorders of tendons and ligaments. Such methods utilize novel compositions including, but not limited to, extraembryonic cytokine-secreting cells (herein referred to as ECS cells), including, but not limited to, Amnion-derived Multipotent Progenitor cells (herein referred to as AMP cells) and conditioned media derived therefrom (herein referred to as Amnion-derived Cellular Cytokine Solution or ACCS), including pooled ACCS, and Physiologic Cytokine Solution (PCS).

6 Claims, No Drawings

METHODS FOR ACCELERATING THE HEALING OF CONNECTIVE TISSUE INJURIES AND DISORDERS

CROSS-REFERENCE TO RELATED APPLICATIONS

This application is a divisional application of U.S. application Ser. No. 13/785,139, filed Mar. 5, 2013, which is a divisional application of U.S. application Ser. No. 13/374,674, filed Jan. 7, 2012, now U.S. Pat. No. 8,642,547 and claims priority under 35 USC §119(e) of U.S. Provisional Application No. 61/460,913, filed Jan. 10, 2011, the entirety entireties of which is are incorporated herein by reference.

FIELD OF THE INVENTION

The field of the invention is directed to methods for accelerating the healing of connective tissue injuries and disorders. In particular, the field of the invention is directed to accelerating the healing of injuries and disorders of tendons and ligaments. Such methods utilize novel compositions including, but not limited to, extraembryonic cytokine-secreting cells (herein referred to as ECS cells), including, but not limited to, Amnion-derived Multipotent Progenitor cells (herein referred to as AMP cells) and conditioned media derived therefrom (herein referred to as Amnion-derived Cellular Cytokine Solution or ACCS, including pooled ACCS), and Physiologic Cytokine Solution (herein referred to as PCS), each alone or in combination with each other and/or other agents.

DESCRIPTION OF RELATED ART

Sharma, P. and Maffulli, N. (Disability and Rehabilitation, 2008; 30(20-22): 1733-1745) discuss emerging treatments for tendinopathy and tendon injury.

BRIEF SUMMARY OF THE INVENTION

It is an object of the instant invention to provide novel methods for accelerating the healing of connective tissue injuries and disorders, in particular, tendon and ligament injury and disease. Such methods for accelerating the healing of connective tissue injuries and disorders utilize novel compositions including extraembryonic cytokine-secreting cells (herein referred to as ECS cells), including Amnion-derived Multipotent Progenitor (AMP) cells, conditioned media and/or cell products derived therefrom (herein referred to as Amnion-derived Cellular Cytokine Solution or ACCS, including pooled ACCS), and Physiologic Cytokine Solution (herein referred to as PCS), each alone and/or in combination with each other and/or with other agents including active and/or inactive agents.

Accordingly, a first aspect of the invention is a method for accelerating the healing of a connective tissue injury or disease patient in need thereof comprising administering to the patient a therapeutically effective amount of one or more compositions selected from the group consisting of extraembryonic cytokine-secreting (ECS) cells, conditioned media derived therefrom, cell lysate derived therefrom, cell products derived therefrom, and Physiologic Cytokine Solution (PCS).

One embodiment of the method of aspect 1 is wherein the connective tissue injury and disease is selected from the group consisting of sprains, strains, contusions, tendinitis/tendinosis, avulsions, bursitis, tenosynovitis, stress fractures and surgery.

Another embodiment of the method of aspect 1 is wherein the ECS cells are Amnion-derived Multipotent Progenitor (AMP) cells.

A specific embodiment of the method of aspect 1 is wherein the conditioned medium is Amnion-derived Cellular Cytokine Solution (ACCS), including pooled ACCS. In a more particular embodiment, the ACCS, pooled ACCS and PCS are formulated for sustained-release.

In another embodiment of the method of aspect 1, the ECS cells, conditioned media derived therefrom, cell lysate derived therefrom or cell products derived therefrom are administered in combination with other agents or treatment modalities.

A specific embodiment of aspect 1 is one is wherein the other agents are active agents. In a particular embodiment the active agents are selected from the group consisting of growth factors, cytokines, inhibitors, immunosuppressive agents, steroids, chemokines, antibodies, antibiotics, antifungals, antivirals, mitomycin C, and other cell types.

Another embodiment of aspect 1 is one wherein the other treatment modalities are selected from the group consisting of rest, ice, compression, elevation, physical therapy and exercise.

Other features and advantages of the invention will be apparent from the accompanying description, examples and the claims. The contents of all references, pending patent applications and issued patents, cited throughout this application are hereby expressly incorporated by reference. In case of conflict, the present specification, including definitions, will control.

DEFINITIONS

As defined herein "isolated" refers to material removed from its original environment and is thus altered "by the hand of man" from its natural state.

As defined herein, a "gene" is the segment of DNA involved in producing a polypeptide chain; it includes regions preceding and following the coding region, as well as intervening sequences (introns) between individual coding segments (exons).

As used herein, the term "protein marker" means any protein molecule characteristic of a cell or cell population. The protein marker may be located on the plasma membrane of a cell or in some cases may be a secreted protein.

As used herein, "enriched" means to selectively concentrate or to increase the amount of one or more materials by elimination of the unwanted materials or selection and separation of desirable materials from a mixture (i.e. separate cells with specific cell markers from a heterogeneous cell population in which not all cells in the population express the marker).

As used herein, the term "substantially purified" means a population of cells substantially homogeneous for a particular marker or combination of markers. By substantially homogeneous is meant at least 90%, and preferably 95% homogeneous for a particular marker or combination of markers.

The term "placenta" as used herein means both preterm and term placenta.

As used herein, the term "totipotent cells" shall have the following meaning. In mammals, totipotent cells have the potential to become any cell type in the adult body; any cell type(s) of the extraembryonic membranes (e.g., placenta).

Totipotent cells are the fertilized egg and approximately the first 4 cells produced by its cleavage.

As used herein, the term "pluripotent stem cells" shall have the following meaning Pluripotent stem cells are true stem cells with the potential to make any differentiated cell in the body, but cannot contribute to making the components of the extraembryonic membranes which are derived from the trophoblast. The amnion develops from the epiblast, not the trophoblast. Three types of pluripotent stem cells have been confirmed to date: Embryonic Stem (ES) Cells (may also be totipotent in primates), Embryonic Germ (EG) Cells, and Embryonic Carcinoma (EC) Cells. These EC cells can be isolated from teratocarcinomas, a tumor that occasionally occurs in the gonad of a fetus. Unlike the other two, they are usually aneuploid.

As used herein, the term "multipotent stem cells" are true stem cells but can only differentiate into a limited number of types. For example, the bone marrow contains multipotent stem cells that give rise to all the cells of the blood but may not be able to differentiate into other cells types.

As used herein, the term "extraembryonic tissue" means tissue located outside the embryonic body which is involved with the embryo's protection, nutrition, waste removal, etc. Extraembryonic tissue is discarded at birth. Extraembryonic tissue includes but is not limited to the amnion, chorion (trophoblast and extraembryonic mesoderm including umbilical cord and vessels), yolk sac, allantois and amniotic fluid (including all components contained therein). Extraembryonic tissue and cells derived therefrom have the same genotype as the developing embryo.

As used herein, the term "extraembryonic cells" or "EE cells" means a population of cells derived from the extraembryonic tissue.

As used herein, the term "extraembryonic cytokine-secreting cells" or "ECS cells" means a population of cells derived from the extraembryonic tissue which have the characteristic of secreting VEGF, Angiogenin, PDGF and TGFβ2 and the MMP inhibitors TIMP-1 and/or TIMP-2 at physiologically relevant levels in a physiologically relevant temporal manner into the extracellular space or into the surrounding culture media. ECS cells have not been cultured in the presence of any non-human animal materials, making them and cell products derived from them suitable for human clinical use as they are not xeno-contaminated. ECS cells may be selected from populations of cells and compositions described in this application and in US2003/0235563, US2004/0161419, US2005/0124003, U.S. Provisional Application Nos. 60/666,949, 60/699,257, 60/742,067, 60/813,759, U.S. application Ser. No. 11/333,849, U.S. application Ser. No. 11/392,892, PCTUS06/011392, US2006/0078993, PCT/US00/40052, U.S. Pat. No. 7,045,148, US2004/0048372, and US2003/0032179, the contents of which are incorporated herein by reference in their entirety. ECS cells have previously been referred to as trophic factor-secreting (TSE) cells.

As used herein, the term "Amnion-derived Multipotent Progenitor cell" or "AMP cell" means a specific population of cells that are epithelial cells derived from the amnion. AMP cells have the following characteristics. They have not been cultured in the presence of any non-human animal materials, making them and cell products derived from them suitable for human clinical use as they are not xeno-contaminated. AMP cells are cultured in basal medium supplemented with human serum albumin. In a preferred embodiment, the AMP cells secrete the cytokines VEGF, Angiogenin, PDGF and TGFβ2 and the MMP inhibitors TIMP-1 and/or TIMP-2. The physiological range of the cytokine or cytokines in the unique combination is as follows: ~5-16 ng/mL for VEGF, ~3.5-4.5 ng/mL for Angiogenin, ~100-165 pg/mL for PDGF, ~2.5-2.7 ng/mL for TGFβ2, ~0.68 µg/mL for TIMP-1 and ~1.04 µg/mL for TIMP-2. AMP cells grow without feeder layers, do not express the protein telomerase and are non-tumorigenic. AMP cells do not express the hematopoietic stem cell marker CD34 protein. The absence of CD34 positive cells in this population indicates the isolates are not contaminated with hematopoietic stem cells such as umbilical cord blood or embryonic fibroblasts. Virtually 100% of the cells react with antibodies to low molecular weight cytokeratins, confirming their epithelial nature. Freshly isolated amnion-derived cells, from which AMP cells are isolated, will not react with antibodies to the stem/progenitor cell markers c-kit (CD117) and Thy-1 (CD90). Several procedures used to obtain cells from full term or pre-term placenta are known in the art (see, for example, US 2004/0110287; Anker et al., 2005, Stem Cells 22:1338-1345; Ramkumar et al., 1995, Am. J. Ob. Gyn. 172:493-500). However, the methods used herein provide improved compositions and populations of cells.

By the term "animal-free" when referring to certain compositions, growth conditions, culture media, etc. described herein, is meant that no non-human animal-derived materials, such as bovine serum, proteins, lipids, carbohydrates, nucleic acids, vitamins, etc., are used in the preparation, growth, culturing, expansion, storage or formulation of the certain composition or process. By "no non-human animal-derived materials" is meant that the materials have never been in or in contact with a non-human animal body or substance so they are not xeno-contaminated. Only clinical grade materials, such as recombinantly produced human proteins, are used in the preparation, growth, culturing, expansion, storage and/or formulation of such compositions and/or processes.

By the term "expanded", in reference to cell compositions, means that the cell population constitutes a significantly higher concentration of cells than is obtained using previous methods. For example, the level of cells per gram of amniotic tissue in expanded compositions of AMP cells is at least 50 and up to 150 fold higher than the number of amnion epithelial cells in the primary culture after 5 passages, as compared to about a 20 fold increase in such cells using previous methods. In another example, the level of cells per gram of amniotic tissue in expanded compositions of AMP cells is at least 30 and up to 100 fold higher than the number of amnion epithelial cells in the primary culture after 3 passages. Accordingly, an "expanded" population has at least a 2 fold, and up to a 10 fold, improvement in cell numbers per gram of amniotic tissue over previous methods. The term "expanded" is meant to cover only those situations in which a person has intervened to elevate the number of the cells.

As used herein, the term "passage" means a cell culture technique in which cells growing in culture that have attained confluence or are close to confluence in a tissue culture vessel are removed from the vessel, diluted with fresh culture media (i.e. diluted 1:5) and placed into a new tissue culture vessel to allow for their continued growth and viability. For example, cells isolated from the amnion are referred to as primary cells. Such cells are expanded in culture by being grown in the growth medium described herein. When such primary cells are subcultured, each round of subculturing is referred to as a passage. As used herein, "primary culture" means the freshly isolated cell population.

As used herein, the term "differentiation" means the process by which cells become progressively more specialized.

As used herein, the term "differentiation efficiency" means the percentage of cells in a population that are differentiating or are able to differentiate.

As used herein, "conditioned medium" is a medium in which a specific cell or population of cells has been cultured, and then removed. When cells are cultured in a medium, they may secrete cellular factors that can provide support to or affect the behavior of other cells. Such factors include, but are not limited to hormones, cytokines, extracellular matrix (ECM), proteins, vesicles, antibodies, chemokines, receptors, inhibitors and granules. The medium containing the cellular factors is the conditioned medium. Examples of methods of preparing conditioned media are described in U.S. Pat. No. 6,372,494 which is incorporated by reference in its entirety herein.

As used herein, the term "Amnion-derived Cellular Cytokine Solution" or "ACCS", including pooled ACCS, means conditioned medium that has been derived from AMP cells that have been cultured in basal media supplemented with human serum albumin. ACCS has previously been referred to as "amnion-derived cellular cytokine suspension".

The term "physiological level" as used herein means the level that a substance in a living system is found and that is relevant to the proper functioning of a biochemical and/or biological process.

As used herein, the term "Physiologic Cytokine Solution" or "PCS" composition means a composition which is not cell-derived and which has physiologic concentrations of one or more factors selected from VEGF, Angiogenin, PDGF and TGFβ2 and at least one MMP inhibitor. Examples of suitable MMP inhibitors include but are not limited to TIMP-1 and TIMP-2. Details on PCS can be found in U.S. Publication No. US-2009-0054339-A1, the contents of which are incorporated herein by reference.

As used herein, the term "pooled" means a plurality of compositions that have been combined to create a new composition having more constant or consistent characteristics as compared to the non-pooled compositions.

The term "therapeutically effective amount" means that amount of a therapeutic agent necessary to achieve a desired physiological effect (i.e. treat connective tissue injury or disease).

The term "lysate" as used herein refers to the composition obtained when cells, for example, AMP cells, are lysed and optionally the cellular debris (e.g., cellular membranes) is removed. This may be achieved by mechanical means, by freezing and thawing, by sonication, by use of detergents, such as EDTA, or by enzymatic digestion using, for example, hyaluronidase, dispase, proteases, and nucleases. In some instances, it may be desirable to lyse the cells and retain the cellular membrane portion and discard the remaining portion of the lysed cells. In other instances, it may be desirable to retain both portions.

As used herein, the term "pharmaceutically acceptable" means that the components, in addition to the therapeutic agent, comprising the formulation, are suitable for administration to the patient being treated in accordance with the present invention.

As used herein, the term "tissue" refers to an aggregation of similarly specialized cells united in the performance of a particular function.

As used herein, the term "therapeutic protein" includes a wide range of biologically active proteins including, but not limited to, growth factors, enzymes, hormones, cytokines, inhibitors of cytokines, blood clotting factors, peptide growth and differentiation factors.

The term "transplantation" as used herein refers to the administration of a composition comprising cells, including a cell suspension or cells incorporated into a matrix or tissue, that are either in an undifferentiated, partially differentiated, or fully differentiated form into a human or other animal.

As used herein, the terms "a" or "an" means one or more; at least one.

As used herein, the term "adjunctive" means jointly, together with, in addition to, in conjunction with, and the like.

As used herein, the term "co-administer" can include simultaneous or sequential administration of two or more agents.

"Treatment," "treat," or "treating," as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition, i.e., arresting its development; (c) relieving and or ameliorating the disease or condition, i.e., causing regression of the disease or condition; or (d) curing the disease or condition, i.e., stopping its development or progression. The population of subjects treated by the methods of the invention includes subjects suffering from the undesirable condition or disease, as well as subjects at risk for development of the condition or disease.

As used herein, the term "accelerated healing" means that the rate at which an injury or wound heals is faster in a treated subject compared to an untreated subject.

DETAILED DESCRIPTION

In accordance with the present invention there may be employed conventional molecular biology, microbiology, and recombinant DNA techniques within the skill of the art. Such techniques are explained fully in the literature. See, e.g., Sambrook et al, 2001, "Molecular Cloning: A Laboratory Manual"; Ausubel, ed., 1994, "Current Protocols in Molecular Biology" Volumes I-III; Celis, ed., 1994, "Cell Biology: A Laboratory Handbook" Volumes I-III; Coligan, ed., 1994, "Current Protocols in Immunology" Volumes I-III; Gait ed., 1984, "Oligonucleotide Synthesis"; Hames & Higgins eds., 1985, "Nucleic Acid Hybridization"; Hames & Higgins, eds., 1984, "Transcription And Translation"; Freshney, ed., 1986, "Animal Cell Culture"; IRL Press, 1986, "Immobilized Cells And Enzymes"; Perbal, 1984, "A Practical Guide To Molecular Cloning."

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

Therapeutic Uses—The compositions of the invention are useful in methods for treating connective tissue injuries and disorders including but not limited to:

Tears and ruptures—Tendons and ligaments are subject to tears and ruptures. Conditions that make a tear or rupture more likely include the injection of steroids into a tendon or ligament, certain diseases (such as gout or hyperparathyroidism), and having type O blood. A tear or rupture can be a serious problem and may result in excruciating pain and permanent disability if untreated. The tears or ruptures are typically treated either surgically or medically depending on the severity of the injury.

Sprains—The joints of the body are supported by ligaments. Ligaments are strong bands of connective tissue that connect one bone to another. A sprain is a simple stretch or tear of the ligaments. The areas most vulnerable to sprains are the ankles, knees, and wrists. Most mild sprains heal with rest, ice, compression, elevation and exercise and/or physical therapy. Moderate sprains may also require a period of bracing. Severe sprains may require surgery to repair torn ligaments.

Strains—The bones are supported by a combination of muscles and tendons. Tendons connect muscles to bones. A strain is the result of an injury to either a muscle or a tendon. The strain may be a simple stretch in the muscle or tendon, or it may be a partial or complete tear in the muscle-and-tendon combination. The recommended treatment for a strain is the same as for a sprain: rest, ice, compression, and elevation, followed by simple exercises and/or physical therapy to relieve pain and restore mobility. For a serious tear, the tissues may need to be repaired surgically.

Contusions—A contusion is a bruise caused by a blow to the muscle, tendon, or ligament. Most contusions are mild and respond well to rest, ice and compression, and elevation of the injured area. If symptoms persist, medical care should be sought to prevent permanent damage to the soft tissues.

Tendonitis/Tendinosis—An inflammation in a tendon or in the covering of the tendon is called tendonitis, which is inflammation of the tendons. Tendonitis is caused by a series of small stresses that repeatedly aggravate the tendon. Tendonitis may be treated by rest to eliminate stress, anti-inflammatory medication, steroid injections, splinting, and exercises and/or physical therapy to correct muscle imbalance and improve flexibility. Persistent inflammation may cause damage to the tendon, which may necessitate surgical correction.

Bursitis—A bursa is a sac filled with fluid that is located between a bone and a tendon or muscle. A bursa allows the tendon to slide smoothly over the bone. Repeated small stresses and overuse can cause the bursa to swell. This swelling and irritation is called bursitis. Many people experience bursitis in association with tendonitis. Bursitis can usually be relieved by rest and possibly with anti-inflammatory medication. Physicians may also inject the bursa with additional medication to reduce the inflammation.

Stress Fractures—When one of the bones is stressed by overuse, tiny breaks in the bone can occur. The injury is termed a stress fracture. Early symptoms may be pain and swelling in the region of the stress fracture. The bones of the lower leg and foot are particularly prone to stress fractures. The fracture may not be seen on initial routine X-rays, requiring a bone scan to obtain the diagnosis. These injuries are treated by rest, activity modification, cast immobilization, and, rarely, by surgery.

Tenosynovitis—Another chronic overuse tendon problem is tenosynovitis, which is an inflammation and/or irritation between a tendon and its surrounding synovial sheath (epitenon). The sheath reduces friction between the tendon and the retinaculum (or, infrequently, a ligament) that binds the tendon close to the joint. The tendon must be able to glide freely within the sheath.

Avulsion—An avulsion is an acute tendon injury resulting from high tensile loads, in which a tendon is forcibly torn away from its attachment site on the bone. In a majority of tensile stress injuries of the musculotendinous unit, fiber tearing occurs at the musculotendinous junction producing a strain. In some other cases these fibers remains intact and the tendon pulls away from its bony attachment site. Avulsion injuries occur in regions where a large muscle attaches at a relatively small site on the bone.

Surgery—Tendon and ligament repair can be performed using local anesthesia, regional anesthesia or general anesthesia. The surgeon makes an incision in the skin over the injured tendon or ligament and the damaged or torn ends of the tendon or ligament are sewn together. If the tendon or ligament has been severely injured, a graft may be required. In this case, a piece of tendon or ligament from another part of the body is often used. If necessary, tendons and ligaments are reattached to the surrounding tissue. The goal of the repair is to bring back normal function of joints or surrounding tissues following the injury. Possible risks include scar tissue formation that prevents smooth movements, partial loss of use in the involved joint, and stiffness of the joint Obtaining and Culturing of Cells ECS cells—Various methods for isolating cells from the extraembryonic tissue, which may then be used to produce the ECS cells of the instant invention are described in the art (see, for example, US2003/0235563, US2004/0161419, US2005/0124003, U.S. Provisional Application Nos. 60/666,949, 60/699,257, 60/742,067, 60/813,759, U.S. application Ser. No. 11/333,849, U.S. application Ser. No. 11/392,892, PCTUS06/011392, US2006/0078993, PCT/US00/40052, U.S. Pat. No. 7,045,148, US2004/0048372, and US2003/0032179).

Identifying ECS cells—Once extraembryonic tissue is isolated, it is necessary to identify which cells in the tissue have the characteristics associated with ECS cells (see definition above). For example, cells are assayed for their ability to secrete VEGF, Angiogenin, PDGF and TGFβ2 and the MMP inhibitors TIMP-1 and/or TIMP-2 into the extracellular space or into surrounding culture media. In some instances, it may be difficult or impossible to detect certain factors using standard assays. This may be because certain factors are secreted by the cells at physiological levels that are below the level of detection by the assay methods. It may also be that the factor(s) is being utilized by the ECS cell and/or by other local cells, thus preventing accumulation at detectable levels using standard assays. It is also possible that the temporal manner in which the factors are secreted may not coincide with the timing of sampling.

AMP cell compositions are prepared using the steps of a) recovery of the amnion from the placenta, b) dissociation of the epithelial cells from the amniotic membrane using a protease, c) culturing of the cells in a basal medium with the addition of a naturally derived or recombinantly produced human protein (i.e. human serum albumin) and no non-human animal protein; d) selecting AMP cells from the epithelial cell culture, and optionally e) further proliferation of the cells, optionally using additional additives and/or growth factors (i.e. recombinant human EGF). Details are contained in US Publication No. 2006-0222634-A1, which is incorporated herein by reference.

Culturing of the AMP cells—The cells are cultured in a basal medium. Such medium includes, but is not limited to, EPILIFE® culture medium for epithelial cells (Cascade Biologicals), OPTI-PRO™ serum-free culture medium, VP-SFM serum-free medium, IMDM highly enriched basal medium, KNOCKOUT™ DMEM low osmolality medium, 293 SFM II defined serum-free medium (all made by Gibco; Invitrogen), HPGM hematopoietic progenitor growth medium, Pro 293S-CDM serum-free medium, Pro 293A-CDM serum-free medium, UltraMDCK™ serum-free medium (all made by Cambrex), STEMLINE® T-cell expansion medium and STEMLINE® II hematopoietic stem cell expansion medium (both made by Sigma-Aldrich), DMEM culture medium, DMEM/F-12 nutrient mixture growth medium (both made by Gibco), Ham's F-12 nutrient mixture growth medium, M199 basal culture medium (both made by Sigma-Aldrich), and other comparable basal media. Such media should either contain human protein or be supplemented with human protein. As used herein a "human protein" is one that is produced naturally or one that is produced using recombinant technology, for example, human serum albumin. In specific embodiments, the basal media is IMDM highly enriched basal medium, STEMLINE® T-cell expansion medium or STEMLINE® II hematopoietic stem cell expansion medium, or OPTI-PRO™ serum-free culture medium, or combinations thereof and the human protein is human serum albumin added at at least 0.5% and up to 10%. In particular embodiments, the human serum albumin is from about 0.5% to about 2%. In a specific embodiment the human serum albumin is at 0.5%. The human serum albumin may come from a liquid or a dried (powder) form and includes, but is not limited to, recombinant human serum albumin, PLASBUMIN® normal human serum albumin and PLASMANATE® human blood fraction (both made by Talecris Biotherapeutics).

In a most preferred embodiment, the cells are cultured using a system that is free of non-human animal products to avoid xeno-contamination. In this embodiment, the culture medium is IMDM highly enriched basal medium, STEMLINE® T-cell expansion medium or STEMLINE® II hematopoietic stem cell expansion medium, OPTI-PRO™ serum-free culture medium, or DMEM culture medium, with human albumin (PLASBUMIN® normal human serum albumin) added up to amounts of 10%.

The invention further contemplates the use of any of the above basal media wherein animal-derived proteins are replaced with recombinant human proteins and animal-derived serum, such as BSA, is replaced with human serum albumin. In preferred embodiments, the media is serum-free in addition to being animal-free.

Optionally, other factors are used. In one embodiment, epidermal growth factor (EGF) at a concentration of between 0-1 µg/mL is used. In a preferred embodiment, the EGF concentration is around 10-20 ng/mL. Alternative growth factors which may be used include, but are not limited to, TGFα or TGFβ2 (5 ng/mL; range 0.1-100 ng/mL), activin A, cholera toxin (preferably at a level of about 0.1 µg/mL; range 0-10 µg/mL), transferrin (5 µg/mL; range 0.1-100 µg/mL), fibroblast growth factors (bFGF 40 ng/mL (range 0-200 ng/mL), aFGF, FGF-4, FGF-8; (all in range 0-200 ng/mL), bone morphogenic proteins (i.e. BMP-4) or other growth factors known to enhance cell proliferation. All supplements are clinical grade.

Generation of Conditioned Medium

ECS cell conditioned medium—is obtained as described below for ACCS, except that ECS cells are used.

Generation of ACCS—The AMP cells of the invention can be used to generate ACCS. In one embodiment, the AMP cells are isolated as described herein and $1 \times 10^6$ cells/mL are seeded into T75 flasks containing between 5-30 mL culture medium, preferably between 10-25 mL culture medium, and most preferably about 10 mL culture medium. The cells are cultured until confluent, the medium is changed and in one embodiment the ACCS is collected 1 day post-confluence. In another embodiment the medium is changed and ACCS is collected 2 days post-confluence. In another embodiment the medium is changed and ACCS is collected 3 days post-confluence. In another embodiment the medium is changed and ACCS is collected 4 days post-confluence. In another embodiment the medium is changed and ACCS is collected 5 days post-confluence. In another embodiment the medium is changed and ACCS is collected 3 days post-confluence. In another preferred embodiment the medium is changed and ACCS is collected 3, 4, 5, 6 or more days post-confluence. Skilled artisans will recognize that other embodiments for collecting ACCS from AMP cell cultures, such as using other tissue culture vessels, including but not limited to cell factories, flasks, hollow fibers, or suspension culture apparatus, or collecting ACCS from sub-confluent and/or actively proliferating cultures, are also contemplated by the methods of the invention. It is also contemplated by the instant invention that the ACCS be cryopreserved following collection. It is also contemplated by the invention that ACCS be lyophilized following collection. It is also contemplated that ACCS be formulated for sustained-release after collection.

The compositions of the invention can be prepared in a variety of ways depending on the intended use of the compositions. For example, a composition useful in practicing the invention may be a liquid comprising an agent of the invention, i.e. ECS cells, including AMP cells and/or ACCS, pooled ACCS, or PCS, in solution, in suspension, or both (solution/suspension). The term "solution/suspension" refers to a liquid composition where a first portion of the active agent is present in solution and a second portion of the active agent is present in particulate form, in suspension in a liquid matrix. A liquid composition also includes a gel. The liquid composition may be aqueous or in the form of an ointment, salve, cream, or the like.

An aqueous suspension or solution/suspension useful for practicing the methods of the invention may contain one or more polymers as suspending agents. Useful polymers include water-soluble polymers such as cellulosic polymers and water-insoluble polymers such as cross-linked carboxyl-containing polymers. An aqueous suspension or solution/suspension of the present invention is preferably viscous or muco-adhesive, or even more preferably, both viscous and muco-adhesive.

Pharmaceutical Compositions—The present invention provides pharmaceutical compositions of ECS cells, including AMP cells and/or ACCS, pooled ACCS, or PCS and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the composition is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Examples of suitable pharmaceutical carriers are described in "Remington's Pharmaceutical Sciences" by E. W. Martin, and still others are familiar to skilled artisans.

The pharmaceutical compositions of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Treatment Kits—The invention also provides for an article of manufacture comprising packaging material and a pharmaceutical composition of the invention contained within the packaging material, wherein the pharmaceutical composition comprises compositions of ECS cells, including AMP cells and/or ACCS, pooled ACCS or PCS. The packaging material comprises a label or package insert which indicates that the ECS cells, including AMP cells and/or ACCS, pooled ACCS, or PCS can be used for treating connective tissue injuries and disorders.

Formulation, Dosage and Administration

Compositions comprising ECS cells, including AMP cells and/or ACCS, pooled ACCS, or PCS may be administered to a subject to provide various cellular or tissue functions, for example, to treat connective tissue injuries and disorders. As used herein "subject" may mean either a human or non-human animal.

Such compositions may be formulated in any conventional manner using one or more physiologically acceptable carriers optionally comprising excipients and auxiliaries. Proper formulation is dependent upon the route of administration chosen. The compositions may be packaged with written instructions for their use in treating connective tissue injuries and disorders or restoring a therapeutically important metabolic function. The compositions may also be administered to the recipient in one or more physiologically acceptable carriers. Carriers for the cells may include but are not limited to solutions of phosphate buffered saline (PBS) or lactated Ringer's solution containing a mixture of salts in physiologic concentrations.

Pharmaceutical compositions useful in the practice of certain embodiments of the invention (i.e. those utilizing topical administration) include a therapeutically effective amount of an active agent with a pharmaceutically acceptable carrier. Such pharmaceutical compositions may be liquid, gel, ointment, salve, slow release formulations or other formulations suitable for administration to connective tissues, including tendons and ligaments. The composition comprises a composition of the invention (i.e. ECS cells, including AMP cells and/or ACCS, pooled ACCS or PCS) and, optionally, at least one pharmaceutically acceptable excipient.

In various embodiments, compositions of the invention can comprise a liquid comprising an active agent in solution, in suspension, or both. The term "suspension" herein includes a liquid composition wherein a first portion of the active agent is present in solution and a second portion of the active agent is present in particulate form, in suspension in a liquid matrix. As used herein, liquid compositions include gels.

Preferably the liquid composition is aqueous. Alternatively, the composition can take form of an ointment. In a preferred embodiment, the composition is an in situ gellable aqueous composition, more preferably an in situ gellable aqueous solution. Such a composition can comprise a gelling agent in a concentration effective to promote gelling upon contact with the body. Suitable gelling agents non-restrictively include thermosetting polymers such as tetra-substituted ethylene diamine block copolymers of ethylene oxide and propylene oxide (e.g., poloxamine 1307); polycarbophil; and polysaccharides such as gellan, carrageenan (e.g., kappa-carrageenan and iota-carrageenan), chitosan and alginate gums. The phrase "in situ gellable" includes not only liquids of low viscosity that can form gels, but also more viscous liquids such as semi-fluid and thixotropic gels that exhibit substantially increased viscosity or gel stiffness upon administration.

Aqueous compositions of the invention have physiologically compatible pH and osmolality. Preferably these compositions incorporate means to inhibit microbial growth, for example through preparation and packaging under sterile conditions and/or through inclusion of an antimicrobially effective amount of an acceptable preservative. Suitable preservatives non-restrictively include mercury-containing substances such as phenylmercuric salts (e.g., phenylmercuric acetate, borate and nitrate) and thimerosal; stabilized chlorine dioxide; quaternary ammonium compounds such as benzalkonium chloride, cetyltrimethylammonium bromide and cetylpyridinium chloride; imidazolidinyl urea; parabens such as methylparaben, ethylparaben, propylparaben and butylparaben, and salts thereof; phenoxyethanol; chlorophenoxyethanol; phenoxypropanol; chlorobutanol; chlorocresol; phenylethyl alcohol; disodium EDTA; and sorbic acid and salts thereof.

The composition can comprise a depot formulation comprising an active agent for administration. The depot formulation comprises a composition of the invention (i.e. ECS cells, including AMP cells and/or ACCS, pooled ACCS, or PCS). The microparticles comprising the compositions can be embedded in a biocompatible pharmaceutically acceptable polymer or a lipid encapsulating agent. The depot formulations may be adapted to release all of substantially all the active material over an extended period of time. The polymer or lipid matrix, if present, may be adapted to degrade sufficiently to be transported from the site of administration after release of all or substantially all the active agent. The depot formulation can be liquid formulation, comprising a pharmaceutical acceptable polymer and a dissolved or dispersed active agent. Upon injection, the polymer forms a depot at the injections site, e.g. by gelifying or precipitating.

The composition can comprise a solid article that can be inserted in a suitable location in the disease or injury site, where the article releases the active agent. Release from such an article is preferably to the tendons and/or ligaments, with which the solid article is generally in intimate contact. Solid articles suitable for implantation generally comprise polymers and can be bioerodible or non-bioerodible. Bioerodible polymers that can be used in preparation of implants carrying a composition in accordance with the present invention include without restriction aliphatic polyesters such as polymers and copolymers of poly(glycolide), poly(lactide), poly(.epsilon.-caprolactone), poly(hydroxybutyrate) and poly(hydroxyvalerate), polyamino acids, polyorthoesters, polyanhydrides, aliphatic polycarbonates and polyether lactose. Illustrative of suitable non-bioerodible polymers are silicone elastomers.

One of skill in the art may readily determine the appropriate concentration, or dose, of the ECS cells, including AMP cells and/or ACCS, or PCS, for a particular purpose. The skilled artisan will recognize that a preferred dose is one which produces a therapeutic effect, such as treating connective tissue injuries and disorders, in a patient in need thereof. Of course, proper doses of the ECS cells, including AMP cells and/or ACCS, pooled ACCS, or PCS, will require empirical determination at time of use based on several variables including but not limited to the severity and type of disease, injury, disorder or condition being treated; patient age, weight, sex, health; other medications and treatments being administered to the patient; and the like. One of skill in the art will also recognize that number of doses (dosing regimen) to be administered needs also to be empirically determined based on, for example, severity and type of disease, injury, disorder or condition being treated. In a preferred embodiment, one dose is sufficient. Other preferred embodiments contemplate, 2, 3, 4, or more doses.

The present invention provides a method of treating connective tissue injuries and disorders by administering to a subject ECS cells, including AMP cells and/or ACCS, or PCS, in a therapeutically effective amount. By "therapeutically effective amount" is meant the dose of ECS cells, including AMP cells and/or ACCS, pooled ACCS, or PCS, which is sufficient to elicit a therapeutic effect. Thus, the concentration of ECS cells, including AMP cells and/or ACCS, pooled ACCS, or PCS, in an administered dose unit in accordance with the present invention is effective in, for example, treating connective tissue injuries and disorders.

In further embodiments of the present invention, it may be desirable to co-administer other agents, including active agents and/or inactive agents, with the ECS cells, including AMP cells and/or ACCS, pooled ACCS, or PCS, to treat connective tissue injuries and disorders. Active agents include but are not limited to cytokines, chemokines, antibodies, inhibitors, antibiotics, anti-fungals, anti-virals, immunosuppressive agents, other cell types, and the like. Inactive agents include carriers, diluents, stabilizers, gelling agents, delivery vehicles, ECMs (natural and synthetic), scaffolds, and the like. When the ECS cells, including AMP cells and/or ACCS, pooled ACCS, or PCS, are administered conjointly with other pharmaceutically active agents, even less of the ECS cells, including AMP cells and/or ACCS, pooled ACCS, or PCS, may be needed to be therapeutically effective.

ECS cells, including AMP cells and/or ACCS, pooled ACCS, or PCS, can be administered by injection into a target site of a subject, preferably via a delivery device, such as a tube, e.g., catheter. In a preferred embodiment, the tube additionally contains a needle, e.g., a syringe, through which the cells and/or ACCS can be introduced into the subject at a desired location.

The timing of administration of ECS cells, including AMP cells and/or ACCS, pooled ACCS, or PCS, will depend upon the type and severity of the connective tissue injury or disease being treated. In a preferred embodiment, the ECS cells, including AMP cells and/or ACCS, pooled ACCS, or PCS, are administered as soon as possible after the connective tissue injury occurs or the disease is diagnosed. In other preferred embodiments, the ECS cells, including AMP cells and/or ACCS, pooled ACCS, or PCS, are administered more than one time following injury or diagnosis.

Also contemplated by the methods of the invention are compositions comprising cells that have been partially or fully differentiated from ECS cells, including AMP cells. Such partially or fully differentiated cell compositions are obtained by treating ECS cells, including AMP cells, with appropriate reagents and under appropriate conditions wherein the cells undergo partial or complete differentiation into, for example, connective tissue cells. Skilled artisans are familiar with conditions capable of effecting such partial or complete differentiation. The cells may be treated under differentiating conditions prior to use (i.e. prior to transplantation, administration, etc.) or simultaneously with use. In certain embodiments, the cells are treated under differentiation conditions before and during use.

Sustained-Release Compositions

The ACCS, pooled ACCS or PCS, maybe formulated as sustained-release compositions. Skilled artisans are familiar with methodologies to create sustained-release compositions of therapeutic agents, including protein-based therapeutic agents such as ACCS, pooled ACCS or PCS.

The sustained-release compositions may be made by any of the methods described herein. For example, multivesicular liposome formulation technology is useful for the sustained-release of protein and peptide therapeutics. Qui, J., et al, (ACTA Pharmacol Sin, 2005, 26(11):1395-401) describe this methodology for the formulation of sustained-release interferon alpha-2b. Vyas, S. P., et al, (Drug Dev Ind Pharm, 2006, 32(6):699-707) describe encapsulating pegylated interferon alpha in multivesicular liposomes. ACCS, including pooled ACCS, and PCS are suitable for use in multivesicular liposome sustained-release formulation.

Nanoparticle technology is also useful for creating sustained-release compositions. For example, Packhaeuser, C. B., et al, (J Control Release, 2007, 123(2):131-40) describe biodegradable parenteral depot systems based on insulin loaded dialkylaminoalkyl-amine-poly(vinyl alcohol)-g-poly(lactide-co-glycolide) nanoparticles and conclude that nanoparticle-based depots are suitable candidates for the design of controlled-release devices for bioactive macromolecules (i.e. proteins). Dailey, L. A., et al, (Pharm Res 2003, 20(12):2011-20) describe surfactant-free, biodegradable nanoparticles for aerosol therapy which is based on the branched polymers DEAPA-PVAL-g-PLGA and conclude that DEAPA-PVAL-g-PLGA are versatile drug delivery systems. ACCS, including pooled ACCS, and PCS are suitable for use in nanoparticle-based sustained-release formulations.

Polymer-based sustained-release formulations are also very useful. Chan, Y. P., et al, (Expert Opin Drug Deliv, 2007, 4(4):441-51) provide a review of the Medusa system (Flamel Technologies), which is used for sustained-release of protein and peptide therapies. Thus far, the Medusa system has been applied to subcutaneous injection of IL-2 and IFN-alpha(2b), in animal models (rats, dogs, monkeys), and in clinical trials in renal cancer (IL-2) and hepatitis C (IFN-alpha(2b)) patients. Chavanpatil, M. D., et al, (Pharm Res, 2007, 24(4):803-10) describe surfactant-polymer nanoparticles as a novel platform for sustained and enhanced cellular delivery of water-soluble molecules. Takeuchi, H., et al, (Adv Drug Deliv Res, 2001, 47(1):39-54) describe mucoadhesive nanoparticulate systems for peptide drug delivery, including liposomes and polymeric nanoparticles. Wong, H. L., et al, (Pharm Res, 2006, 23(7):1574-85)

describe a new polymer-lipid hybrid system which has been shown to increase cytotoxicity of doxorubicin against multidrug-resistant breast cancer cells. ACCS, including pooled ACCS, and PCS are suitable for use in the aforementioned sustained-release formulation methodologies.

In addition, other sustained-release methodologies familiar to skilled artisans, while not specifically described herein, are also suitable for use.

Skilled artisans will recognize that any and all of the standard methods and modalities for treating connective tissue injuries and disorders currently in clinical practice and clinical development are suitable for practicing the methods of the invention. Routes of administration, formulation, co-administration with other agents (if appropriate) and the like are discussed in detail elsewhere herein.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1: Preparation of AMP Cell Compositions

Amnion epithelial cells were dissociated from starting amniotic membrane using the dissociation agents PXXIII. The average weight range of an amnion was 18-27 g. The number of cells recovered per g of amnion was about $10\text{-}15 \times 10^6$ for dissociation with PXXIII.

Method of obtaining selected AMP cells—Amnion epithelial cells were plated immediately upon isolation from the amnion. After ~2 days in culture non-adherent cells were removed and the adherent cells were kept. This attachment to a plastic tissue culture vessel is the selection method used to obtain the desired population of AMP cells. Adherent and non-adherent AMP cells appear to have a similar cell surface marker expression profile but the adherent cells have greater viability and are the desired population of cells. Adherent AMP cells were cultured in basal medium supplemented with human serum albumin until they reached ~120,000-150,000 cells/cm$^2$. At this point, the cultures were confluent. Suitable cell cultures will reach this number of cells between ~5-14 days. Attaining this criterion is an indicator of the proliferative potential of the AMP cells and cells that do not achieve this criterion are not selected for further analysis and use. Once the AMP cells reached ~120,000-150,000 cells/cm$^2$, they were collected and cryopreserved. This collection time point is called p0.

Example 2: Generation of ACCS

The AMP cells of the invention can be used to generate ACCS, including pooled ACCS. The AMP cells were isolated as described above and ~1×10$^6$ cells/mL were seeded into T75 flasks containing ~10 mL culture medium as described above. The cells were cultured until confluent, the medium was changed and ACCS was collected 3 days post-confluence. Optionally, the ACCS is collected again after 3 days, and optionally again after 3 days. Skilled artisans will recognize that other embodiments for collecting ACCS from confluent cultures, such as using other tissue culture vessels, including but not limited to cell factories, flasks, hollow fibers, or suspension culture apparatus, etc. are also contemplated by the methods of the invention (see Detailed Description above). It is also contemplated by the instant invention that the ACCS be cryopreserved, lyophilized, irradiated or formulated for sustained-release following collection. It is also contemplated that ACCS be collected at different time points (see Detailed Description for details).

Example 3: Generation of PCS Compositions

The following PCS compositions are produced by combining the indicated cytokine or factor at physiologic levels in a carrier:

Composition A: VEGF and TIMP-1; Composition B: VEGF, Angiogenin and TIMP-1; Composition C: VEGF, Angiogenin, PDGF-BB and TIMP-1; Composition D: VEGF, Angiogenin, PDGF-BB, TGFβ2 and TIMP-1; Composition E: VEGF and TIMP-2; Composition F: VEGF, Angiogenin and TIMP-2; Composition G: VEGF, Angiogenin, PDGF-BB and TIMP-2; Composition H: VEGF, Angiogenin, PDGF-BB, TGFβ2 and TIMP-2; Composition I: VEGF, TIMP-1 and TIMP-2; Composition J: VEGF, Angiogenin, TIMP-1 and TIMP-2; Composition K: VEGF, Angiogenin, PDGF-BB, TIMP-1 and TIMP-2; Composition L: VEGF, Angiogenin, PDGF-BB, TGFβ2, TIMP-1 and TIMP-2; Composition M: Angiogenin and TIMP-1; Composition N: Angiogenin, PDGF-BB and TIMP-1; Composition O: Angiogenin, PDGF-BB, TGFβ2 and TIMP-1; Composition P: Angiogenin and TIMP-2; Composition Q: Angiogenin, PDGF-BB and TIMP-2; Composition R: Angiogenin, PDGF-BB, TGFβ2 and TIMP-2; Composition S: Angiogenin, PDGF-BB, TGFβ2, TIMP-1 and TIMP-2; Composition T: PDGF-BB and TIMP-1; Composition U: PDGF-BB, TGFβ2 and TIMP-1; Composition V: PDGF-BB and TIMP-2; Composition W: PDGF-BB, TGFβ2 and TIMP-2; Composition X: PDGF-BB, TIMP-1 and TIMP-2; Composition Y: PDGF-BB, TGFβ2, TIMP-1 and TIMP-2. A preferred composition is Composition L.

Compositions A-Y optionally contains Thymosin β4. Skilled artisans will recognize that in certain embodiments other MMP inhibitors (i.e. TIMP-3, TIMP-4 or synthetic MMP inhibitors) may be suitable (J. Frederick Woessner, Jr., J. Clin. Invest. 108(6): 799-800 (2001); Brew, K., et al, Biochim Biophys Acta. 2000 Mar. 7; 1477(1-2):267-83).

VEGF, Angiogenin, PDGF-BB, TGFβ2, TIMP-1 and TIMP-2 are added at the following physiologic levels: ~5-16 ng/mL for VEGF, ~3.5-4.5 ng/mL for Angiogenin, ~100-165 pg/mL for PDGF, ~2.5-2.7 ng/mL for TGFβ2, ~0.68 μg mL for TIMP-1 and ~1.04 μg/mL for TIMP-2. VEGF may be obtained from Invitrogen, catalog #PHG0144, PHG0145, PHG0146, PHG0141 or PHG0143; Angiogenin may be obtained from R&D Systems, catalog #265-AN-050 or 265-AN-250; PDGF-BB may be obtained from Invitrogen, catalog #PHG0044, #PHG0045, #PHG0046, #PHG0041, #PHG0043; TGFβ2 may be obtained from Invitrogen, catalog #PHG9114; TIMP-1 may be obtained from R&D Systems, catalog #970-TM-010; and TIMP-2 may be obtained from R&D Systems, catalog #971-TM-010. VEGF, Angiogenin, PDGF-BB, TGFβ2, TIMP-1 and TIMP-2 are added to a carrier such as normal saline, PBS, lactated Ringer's solution, cell culture media, water or other suitable aqueous solution known to skilled artisans.

Example 4: Generation of Sustained-Release Compositions

Sustained-release compositions of ACCS, including pooled ACCS, or PCS, are produced by combining ACCS, including pooled ACCS, or PCS compositions with any of the sustained-release formulation technologies described herein (see Detailed Description) or otherwise familiar to skilled artisans.

Example 5: Use of AMP Cells and ACCS in an Animal Model of Connective Tissue Injury The objective of this study was to assess the effect of AMP cells and ACCS on Achilles tendon healing using a rat model.

Materials and Methods

Animals: One-hundred and twenty six female Sprague-Dawley rats (Charles River, Cambridge, Mass.), weighing approximately 300 g and 10 weeks old, were used in this experiment. The animals were kept two per cage and given food and water ad libitum. Each cage (n=63) was randomly assigned to three different groups: Group A—Saline, Group B—ACCS and Group C—AMP cells. The study was approved by the HMA Standing Committee on Animals, and all institutional guidelines for the care and treatment of laboratory animals were adhered to.

Surgical Procedure: Rats were anesthetized with ketamine (60 mg/kg i.p.) and xylazine (10 mg/kg i.p.) and maintained using isoflurane gas (1-2%) via nose cone. The right hind leg was then shaved using a hair clipper, and sterilized using 70% alcohol, betadine, and 70% alcohol sequentially. Using sharp dissection, the Achilles tendon was exposed and transected at its' midpoint. Both free ends were then injected with either 100 μl of Saline, ACCS, or 100.000 AMP cells diluted in 100 μl PBS. Tendons were then sutured together using 6-0 ethylene braided sutures (Ethicon, Somerville, N.J.) using a Modified-Kessler Technique Skin was closed using 6-0 nylon sutures (Ethicon). Legs were then wrapped in petroleum gauze and then immobilized using a cast that was applied from the toes to the abdomen, achieving three-point stability (ankle-knee-hip) (Scotchcast, 3M). Rats were then returned to their cage and allowed to heal for either 1, 2, or 4 weeks. Rats were observed daily for signs of appetite, pain, infection, swelling, and muscle paralysis. All casts were removed at 1 week. Animals were sacrificed by isoflurane overdose (10%) and the Achilles tendons were dissected free from the extraneous soft tissue and harvested together with the calcaneal bone and parts of the gastrocnemius and soleus muscle complex. The mechanical testing specimens were immediately frozen at −70° C. Specimens for histology were dissected in a similar manner without the calcaneus. Contralateral uninjured tendons from each animal were harvested as controls.

Mechanical testing: On the day of evaluation, specimens were thawed to room temperature and prepared for tensile testing. For clamping, the muscle was carefully scraped off the proximal tendon by blunt dissection to produce a fan of tendon fibers that were then gripped using a large Pennington clamp (Johnson & Johnson, New Brunswick, N.J.) and 1200 grit moist sandpaper (Home Depot, Boston, Mass.). The distal end of the tendon was then gripped using another Pennington clamp just proximal to the calcaneal insertion. The two Pennington clamps were then, in turn, secured in a materials testing machine (Instron 5565, Norwood, Mass.) vertically using pneumatic grips with serrated jaw-faces. Tendons width, thickness and length (distance between Pennington clamp ends) were then recorded using a slide caliper. The cross-sectional area was calculated assuming a rectangular geometry. During tissue preparation and mounting in the materials testing machine, the tendons were kept moist using gauze with saline. Tendons were initially subjected to 3 pre-conditioning cycles to 2% extension to remove any hysteresis. The machine then immediately pulled the specimen at a constant speed of 2 mm/s until failure. The force exerted on the specimen was measured using a 100N load cell (Instron) and all data was collected from Blue-Hill 2 software (Instron). Data was then transferred to an Excel sheet and analyzed for Breaking Strength (defined as force to rupture, N), Ultimate Tensile Strength (defined as maximum stress or force per unit area, MPa), % Strain (defined as change in length over initial length mm/mm) and Young's Modulus (a measure of a material's elasticity, MPa). After mechanical testing, specimens were re-frozen at −70° C. for further evaluation.

Histology: The tendons were immersed in formalin for 24 h and then rinsed in PBS. Tendons were then cut through the sagittal plane for histological evaluation. Paraffin embedded sections were then mounted onto slides and stained with H&E and Masson's Trichrome using standard methods.

Statistical analysis: Data was assumed to be parametric and analysed using two-way analysis of variance (ANOVA) with treatment group and time as independent factors. A Bonferroni post-test was used to correct p-values and minimize type I errors. A p-value of less than 0.05 will be considered statistically significant. All analyses were done using (GraphPad Prism 5 for Windows).

Results:

Young's Modulus is a measure of the relative stiffness/elasticity of a material. The closer the Young's Modulus of a healed tendon is to that of a normal, uninjured tendon, the more similarly it will behave under mechanical stress. Excessive stiffness (by two or more orders of magnitude) over normal is not desirable as the tendon's will display a diminished ability to dissipate energy and may become brittle and tear. In this experiment, the tendons treated with AMP cells and allowed to heal for 4 weeks exhibited a statistically significant (p=0.1%) improvement over both saline-treated and ACCS-treated tendons at the same time point. In fact, AMP-treated tendons were very close to untreated tendon by this measurement. Even at the 2 week time point, a trend in the same direction was observed. The 1 week time point did not reveal any trend.

Ultimate Tensile Strength is a measure of the maximum stress that a material can withstand while being stretched or pulled. In this experiment, a definite trend for improved strength was observed with the AMP cell-treated tendons starting at the 2 week time point and continuing to improve at the 4 week time point. However, this positive trend was not statistically significant.

Cross-sectional Area measures the transverse area of the tendon as it heals. The greater the tendon area, the greater the amount of new tissue generated. This is a positive finding, particularly during the early phase of the healing process as it provides better quality of healing giving the tendon greater strength. H&E and Trichrome histologies of the tendons revealed that the AMP cell-treated tendons at the 4 week time point had a considerably greater transverse cross-sectional area than either saline or ACCS.

Breaking strength measures the ability of a material to resist breaking or rupture from a tension force. In these experiments, breaking strength did not exhibit any discernible difference. However, at 2 weeks, more tissues had healed to the point where they could undergo analysis by tensiometry in both the ACCS and AMPs groups, suggesting there was an earlier improvement in healing when treated with ACCS and AMPs as compared with saline.

Preliminary conclusions are 1) it appears that the 1 week time point is too soon and not enough healing has occurred for any meaningful measurements to be taken by any of the methods utilized; 2) tissues treated with both ACCS and AMPS had better healing at 2 weeks; 3) the AMP cells appear to provide the greatest effect, especially at the 4 week time point. It is theorized that this is because the cells provide a continuous supply of the necessary secreted factors, while the ACCS is essentially a single dose. Future experiments will test sustained-release delivery of ACCS; 3) future experiments should include later time points, such a 6 or 8 weeks, to determine if improvement continues longer after 4 weeks; 4) AMP cell-treated tendons demonstrated a more rapid healing rate and restoration of normal material properties especially with respect to Young's Modulus.

The present invention may be embodied in other specific forms without departing from the spirit or essential attributes thereof. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Throughout the specification various publications have been referred to. It is intended that each publication be incorporated by reference in its entirety into this specification.

What is claimed is:

1. A method for accelerating the healing of tendon and ligament injuries or disorders in a patient in need thereof comprising administering to the patient a therapeutically effective amount of Physiologic Cytokine Solution (PCS), wherein the PCS consists of VEGF, Angiogenin, PDGF-BB, TGFβ2, TIMP-1 and TIMP-2 in a carrier.

2. The method of claim 1 wherein the tendon or ligament injury and disorder is selected from the group consisting of tears, ruptures, sprains, strains, contusions, avulsions, bursitis, tenosynovitis, stress fractures and surgery.

3. The method of claim 1 wherein the PCS is administered in combination with other agents or treatment modalities.

4. The method of claim 3 wherein the other agents are active agents.

5. The method of claim 4 wherein the active agents are selected from the group consisting of growth factors, cytokines, inhibitors, immunosuppressive agents, steroids, chemokines, antibodies, antibiotics, antifungals, antivirals, mitomycin C, and cells.

6. The method of claim 3 wherein the other treatment modalities are selected from the group consisting of rest, ice, compression, elevation, exercise and physical therapy.

* * * * *